(12) United States Patent
Islava

(10) Patent No.: US 6,170,486 B1
(45) Date of Patent: Jan. 9, 2001

(54) HEAD IMMOBILIZER

(76) Inventor: Steven T. Islava, 315 Marigold, Corona del Mar, CA (US) 92625

( * ) Notice: Under 35 U.S.C. 154(b), the term of this patent shall be extended for 0 days.

(21) Appl. No.: 09/070,892

(22) Filed: Apr. 30, 1998

(51) Int. Cl.$^7$ .................................................. A61B 19/00
(52) U.S. Cl. ................................ 128/869; 128/870; 5/637
(58) Field of Search ..................................... 128/845, 846, 128/869, 870, 876; 5/622, 628, 633, 637; 602/19

(56) References Cited

U.S. PATENT DOCUMENTS

| | | | | |
|---|---|---|---|---|
| 4,422,454 | * | 12/1983 | English ................................. | 128/870 |
| 4,601,075 | * | 7/1986 | Smith ................................... | 128/870 |
| 4,979,520 | * | 12/1990 | Boone .................................. | 128/876 |
| 5,014,520 | * | 5/1991 | Williams ............................... | 128/870 |
| 5,211,185 | * | 5/1993 | Garth ................................... | 128/876 |
| 5,265,625 | * | 11/1993 | Bodman ............................... | 128/870 |

* cited by examiner

*Primary Examiner*—Michael A. Brown
(74) *Attorney, Agent, or Firm*—Hogan & Hartson, L.L.P.

(57) ABSTRACT

An improved head immobilizer comprises a head support position for placement beneath an injured patient's head, two head support blocks and a forehead strap. The head support cushion is located beneath the head of a patient on a backboard. After the head support cushion is optimally positioned in reference to the patient, an adhesive system is activated to affix the cushion to the backboard. The head support blocks are placed on either side of the patient's head to immobilize it and are held in position by a hook in loop fastening system. Finally, a forehead strap is stretched from on block to the other across the patient's forehead to more completely immobilize the patient. The strap also uses a hook in loop fastener to attach to the head support blocks.

9 Claims, 3 Drawing Sheets

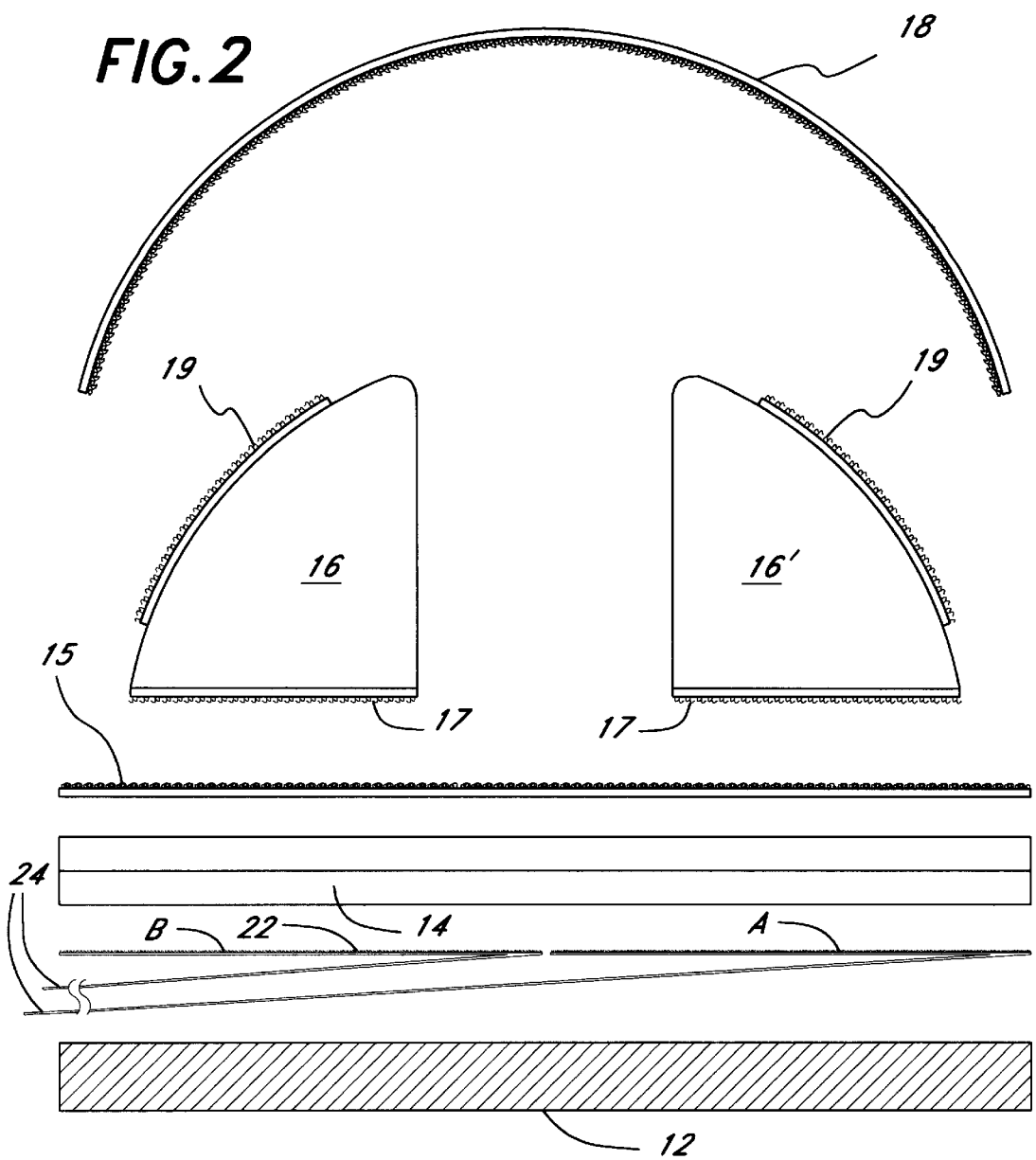

HEAD IMMOBILIZER

BACKGROUND OF THE INVENTION

1. Field of the Invention

The field of the present invention is that of devices and apparatus used for emergency medical care and is more particularly directed to devices used to immobilize accident victims during transit to a hospital.

2. Introduction and Description of Related Art

When a person receives a traumatic injury from an automobile accident or similar mishap, the person's survival often depends on rapid attention from emergency medical personnel followed by immediate transfer to a properly equipped hospital. The emergency medical personnel who are first at the scene of the accident are responsible for treating any immediately life-threatening injuries and for stabilizing the patient for immediate transport to the hospital. One of the most vexing problems faced by these workers is that of neck and back injuries to the victim. Without an x-ray it is often impossible to determine the extent, if any, of the damage. If the spine is damaged, the very act of moving the patient may exacerbate the problem and lead to more extensive spinal injury. There has been some controversy over the best way to treat these injuries prior to transport. Some authorities recommended immobilizing the neck and back in the orientation in which the patient was found. Other authorities favored moving the patient into a neutral position prior to immobilization. Today most practitioners follow the second option and immobilize the patient in a neutral position.

A number of devices and procedures have been developed to immobilize accident victims in a neutral position and allow transport with little or no danger of causing additional spinal damage. The common factor in most of these devices is the simple expedient of firmly attaching the patient to the surface of an stiff, inflexible "board" (backboard) which acts as a stretcher to allow the patient to be carried without allowing any flexing of the patients potentially injured back and neck. Because the patient's neck is so commonly injured in automobile accidents special attention is paid to immobilizing this particularly fragile portion of human anatomy.

Typical of the many immobilizing devices is the Cervical Immobilizer shown in U.S. Pat. No. 4,297,994 to Bashaw. This device consists of two rectangular head blocks attached together by a flexible band rather like ear muffs. These blocks are equipped with hook in loop fastening material (e.g., VELCRO®) to removably attach the blocks to a base unit which is attached to patient support board (backboard) with a number of adjustable hooks and straps. After the base unit it located beneath the patient's head, the two head blocks are located on either side of the patent's head to immobilize it. The flexible band between the blocks contacts the top of the patients head an while additional forehead strap and chin strap can be added to further immobilize the patient's head. One drawback of the large rectangular blocks of this device are that they obscure the patient's ears so that they cannot be readily examined for signs of bleeding and other signs of internal brain injury.

U.S. Pat. No. 4,905,712 to Bowlin et al. solves part of this problem by providing openings through the head blocks so that the patient's ears can be readily examined. This device further has a stretchable base pad which is stretchingly fit to the backboard, thereby obviating the need for various hooks and other attachment devices. After the head blocks are positioned to immobilize the patient's head, they are locked down by straps that are attached to the base pad and pass over the head blocks from one side to the other.

Another version of this type of head immobilizer is taught in U.S. Pat. No. 5,657,766 to Durham which teaches a main board attached to a backboard by means of straps. Head restraining blocks are fixable to the main board by means of a hook in loop fastener system. The straps that stabilize the main board also restrain the patient's head. The blocks are of low profile leaving the patient's ears exposed for ready medical examination.

The prior art also teaches a number of other variations of head supporting blocks. There are a number of devices intended to simplify the restraint systems even further and greatly reduce the overall bulk. Generally, these systems employ cardboard or some similar material to provide disposable restraint systems. U.S. Pat. No. 5,305,754 to Honeywell et al. discloses a device in which cardboard strips are folded to form a hollow triangular head support. U.S. Pat. No. 5,211,185 to Garth et al. discloses a rather minimalist restraint system where a cardboard foundation portion is attached to a backboard and supports a U-shaped cardboard piece that surrounds and supports the patient's head.

The prior art devices range from overly complex devices that require considerable manipulation to engage straps, etc. to very simple cardboard devices that may not provide adequate rigidity and support. The present invention aims to provide an inexpensive and simple device that is easy to use and yet provides exemplary head support and cervical rigidity.

BRIEF DESCRIPTION OF THE DRAWINGS

The objects and features of the present invention, which are believed to be novel, are set forth with particularity in the appended claims. The present invention, both as to its organization and manner of operation, together with further objects and advantages, may best be understood by reference to the following description, taken in connection with the accompanying drawings.

FIG. 2 shows an exploded cross-section of the device of FIG. 1;

FIG. 2B shows an alternative arrangement of the protective paper used in the device of FIG. 2;

DETAILED DESCRIPTION OF THE PREFERRED EMBODIMENTS

The following description is provided to enable any person skilled in the art to make and use the invention and sets forth the best modes contemplated by the inventor of carrying out his invention. Various modifications, however, will remain readily apparent to those skilled in the art, since the general principles of the present invention have been defined herein specifically to provide an improved head stabilization system wherein a head support is positioned and attached to a backboard, head support blocks are adhered to the head support and a forehead strap is adhered to the head support blocks.

Figure 1:
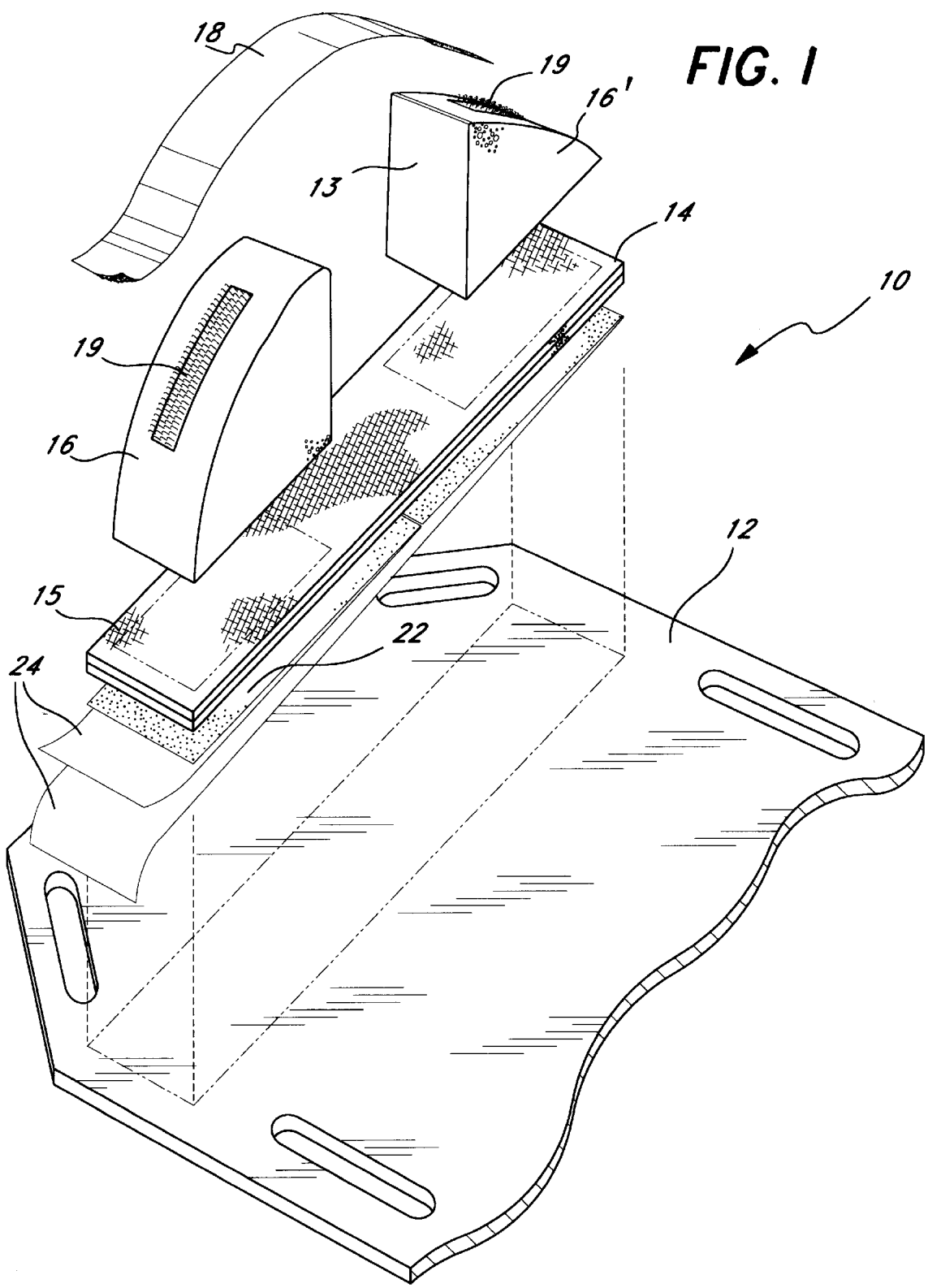
FIG. 1 shows an exploded view of the present invention in relation to a backboard used for patient transport.

FIG. 1 shows an exploded view of the present invention which is generally denominated as 10 shown in relation to the end of a backboard 12. The device also comprises a head support cushion 14 which is a rectangular piece of plastic foam about 2 cm in thickness. It is known that a 2 cm elevation is optimal for cervical immobilization to minimize the degree of spinal flexion (see, "Optimal Positioning for Cervical Immobilization, *Annals of Emergency Medicine* 28:301–08 (1996)). The preferred foam material for the present invention is a cross-linked polyethylene foam although other plastic foams such as polyurethane foam can also be used. Attached to a lower surface of the head support cushion 14 is an adhesive layer 22 covered by removable protective paper 24. Two head support blocks 16, 16' are intended to press up against the side of a patients head, thereby preventing side to side motion. The blocks are cut from plastic foam, such as cross-linked polyethylene foam, and have flat inner faces 13 intended to tightly contact the sides of the patient's head. A strap 18 is equipped with hook in loop fastener and is intended to attach to hook in loop tabs 19 on the outer faces of the head blocks 16, 16'.

As shown in cross-sectional view in FIG. 2, the lower surfaces of the head blocks 16, 16' are equipped with layers of hook in loop fastener 17 which is intended to mate with a layer 15 of hook in loop fastener material on an upper surface of the head support cushion 14. The strap 18 then spans the two tabs 19 one on either head support block 16, 16'. The adhesive layer 22 is intended to strongly attach the head support cushion 14 to the backboard 12. As shown in FIG. 2 the protective paper 24 covers the adhesive layer 22 and prevents the head support cushion 14 from adhering to the backboard 12 or to any structure that comes in contact with it. The protective paper 24 is configured so that pulling the exposed ends causes the protective paper 24 to peal off the adhesive layer 22 uncovering it so that it can adhere to the backboard 12. Depending on the specific design the protective paper 24 can be configured to be pulled from one side or from two sides. In FIG. 2 the protective paper 24 is arranged so both strips can be pulled from one side. In use paper strip A is first pulled to uncover the adhesive layer 22 at the end of the head support cushion 14. If only a small area of adhesive layer 22 is uncovered, it is possible to readily adjust the position of the head support cushion 14. Then strip A is pulled all the way out so that about half of the adhesive layer is uncovered. This provides sufficient adhesive area to firmly affix the head support cushion 14. Finally, strip B is pulled out uncovering the remaining adhesive area and making attachment of the head support cushion 14 to the backboard 12 complete. The unit illustrated in FIG. 2 is arranged so that the protective paper 24 is optimally arranged for a right-handed person. By flipping the head support cushion 14 around the configuration is optimal for a left-handed person.

The one ended arrangement of the protective paper 24 facilitates placement of components and assembly of the device around a patient's head so that firm head support is achieved with no need repeatedly to move the patient's head with the concomitant danger of aggravating any neck or spine injury. An alternative configuration of the protective paper 24 is to have the strips A and B graspable from opposite ends of the head support cushion 14 as shown in FIG. 2B.

Figure 3:
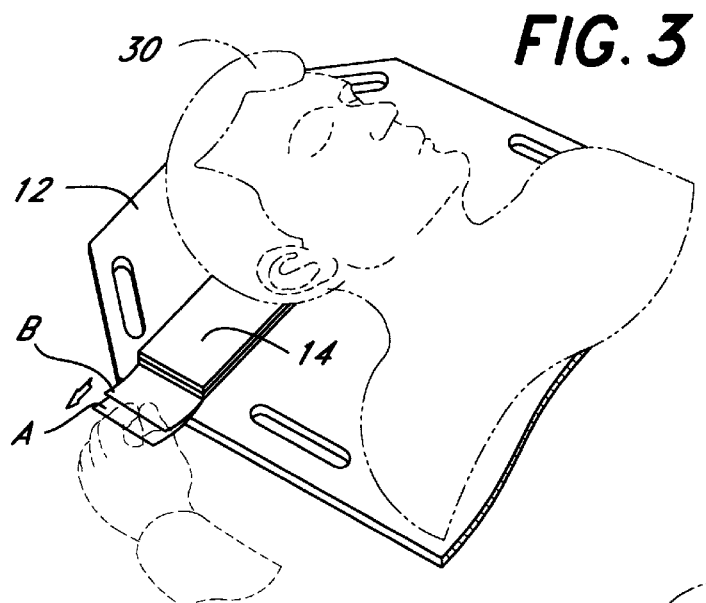
FIG. 3 shows a first step in use of the present invention; namely a head support is placed beneath a patients head and attached to a backboard.
Figure 4:
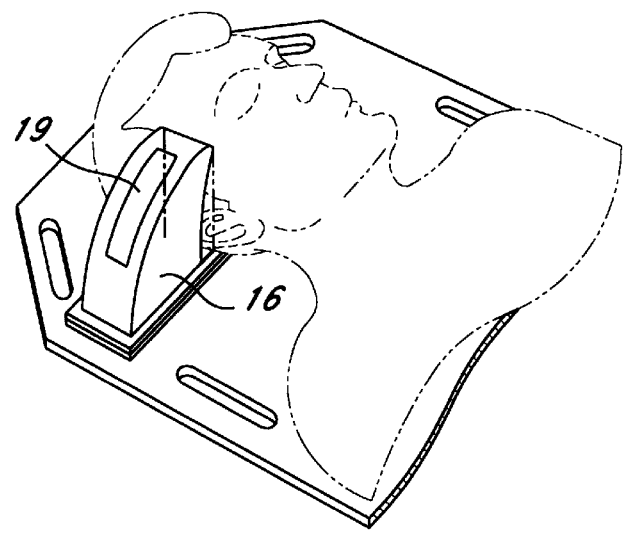
FIG. 4 shows a second step in use of the present invention wherein head support blocks at placed at either side of the patient's head.
Figure 5:
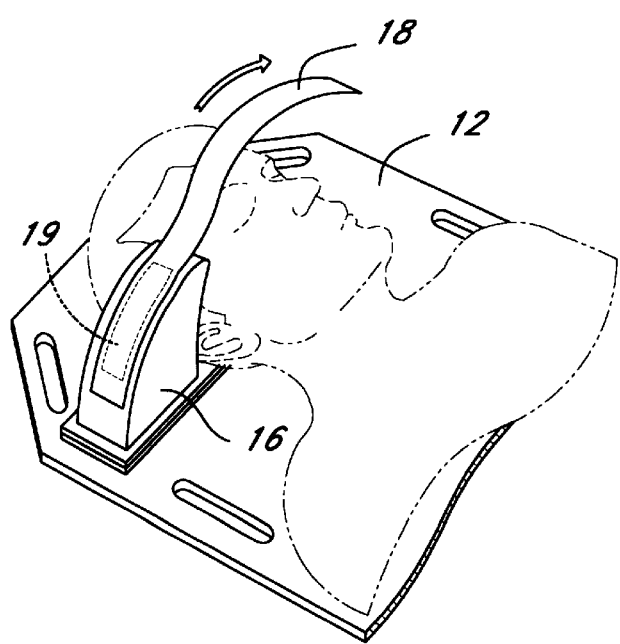
FIG. 5 shows a thirds step in use of the present invention wherein a forehead strap is stretched from head support block to head support block to stabilize the patient's head.

FIGS. 3–5 illustrate the steps in using the present invention. In a first step (not shown) the injured patient 30 is transferred to the backboard 12 and arranged in a safe posture for transport (e.g. lying face up). Then the head support cushion 14 is arranged symmetrically beneath the patient's head. Tests have shown that the approximate two centimeter thickness of the head support cushion 14 precisely elevates the patient's head for maximal safety and comfort. Because of the protective paper 24, the head support cushion 14 can be readily slid around to place it in the optimal position. When this position is attained, strip A is gradually pulled out allowing the left hand (in reference to the patient) end of the head support cushion 14 to firmly adhere to the backboard 12. The rest of strip A is then pulled out followed by strip B so that attachment of the lead support cushion 14 to the backboard 12 is complete. The adhesive used in layer 22 is sufficiently strong that that there is no possibility of accidentally dislodging the head support cushion. If the alternative structure shown in FIG. 2B is used, the center portion of the support cushion 14 is the first area to adhere to the backboard 12.

With the head support cushion 14 in position it is simple to place the right head support block 16 and the left head support block 16' on either side of the patient's head so that the head is firmly pinned between the blocks 16, 16'. The head support blocks are sufficiently wide to give good support but sufficiently narrow to leave the patient's ears uncovered so that the ears can be readily observed for internal bleeding and other signs of trauma. The hook in loop fastener 17 on the lower surfaces of the head support blocks interacts strongly with the complementary hook in look fastener 15 on the upper surface of the head support cushion 14. The hook in loop fastener makes it virtually impossible to slide the head support blocks 16, 16' laterally so that they provide superb support to the patient's head. However, it is still possible to peal the head support blocks 16, 16' away from the head support cushion 14 if it is necessary to reorient them.

Finally, as shown in FIG. 5 the forehead strap 18 is adhered to the fastener tab 19 on one head support block and pulled tautly across the patients forehead and adhered to the tab 19 on the second head support block. The strap 18 prevents the patient's head from moving or bouncing even if the backboard 14 is accidentally dropped or if the ambulance carrying the patient goes over a big bump.

Considerable experimentation has been used to select the adhesives and hook in loop fasteners used in the present invention. Of course, the invention is not inherently altered by using other fastening means. For example, adhesive layer 22 could be replaced by hook in loop fastener; however, this arrangement would make it more difficult to precisely position the head support cushion 14. The incremental uncovering of adhesive layer 22 affords the ability to adjust the precise position of the head support cushion 14. Further, if hook in loop material was permanently in place on the backboard 12, it might become worn and weakened after repeated use. The backboard 12 is more or less permanent whereas the head support system of the present invention is a one use disposable item. Similarly, the hook in loop fastener on the head support blocks 16, 16' and the upper surface of the head support cushion 14 could be replaced by adhesives. Such a configuration, however, has the disadvantage of making it more difficult to adjust the position of the head support blocks; further it would tend to trap the patient's hair in the adhesive. Some other head support systems use adhesive tape to hold down the patient's head; inadvertent hair capture is always a problem with these devices. Finally, the forehead strap 18 could readily be mechanically attached to the head support blocks by posts, screws, hooks or the like. A buckle or similar device could be supplied to adjust the strap length. All of these alternative tend to be more cumbersome to use in an emergency situation than the preferred hook in loop fastener although they do represent viable alternative embodiments. Similarly, the invention encompasses other temporary fastening means for attaching the head support cushion 14 or the head support blocks 16, 16' such as magnetic fastening systems.

Many alterations and modifications may be made by those having ordinary skill in the art without departing from the spirit and scope of the present invention. The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself. The definitions of the words or elements of the following claims are, therefore, defined in this specification to include not only the combination of elements which are literally set forth, but all equivalent structure, material or acts for performing substantially the same function in substantially the same way to obtain substantially the same result.

In addition to the equivalents of the claimed elements, obvious substitutions now or later known to one with ordinary skill in the art are defined to be within the scope of the defined elements. The claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope and spirit of the invention. The illustrated embodiment has been set forth only for the purposes of example and that should not be taken as limiting the invention. Therefore, it is to be understood that, within the scope of the appended claims, the invention may be practiced other than as specifically described herein.

I claim:

1. A head immobilizer system for holding a patient's head firmly to a backboard, the system comprising:

a head support cushion for elevating a patient's head by at least one centimeter;

means on a lower surface of the support cushion for attaching the support cushion to a back support board;

a region of hook in loop fastening material on an upper surface of the support cushion;

two head support blocks for supporting a left side and a right side of a patient's head leaving a patient's ears uncovered, a layer of hook in loop fastening material on each head support block, complementary to the hook in loop fastening material on the upper surface of the support cushion, for repositionably attaching the blocks to the support cushion; and a strap for further immobilizing a patient's head by extending from an upper end of a first head support block across a patient's forehead to an upper end of a second head support block, the strap bearing hook in loop fastening material complementary to hook in loop fastening material on the upper ends of the head support blocks for affixing the strap to the blocks.

2. The system of claim 1, wherein the layer of adhesive is covered by a protection strip that can be pulled to uncover the layer after the support cushion is correctly located without disturbing the support cushion.

3. The system of claim 1, wherein the means for attaching is an adhesive layer.

4. The system of claim 3, wherein the adhesive layer is covered by a protection strip that can be pulled to uncover the adhesive layer after the support cushion is correctly located without disturbing the head support cushion.

5. The system of claim 1, wherein the support cushion is between 1 and 2 cm in thickness.

6. A head immobilizer system for holding a patient's head firmly to a backboard, the system comprising:

a head support cushion for placement beneath a patient's head to cause an elevation of at least one centimeter, the support cushion having on a lower surface a layer of adhesive for attaching the support cushion to the back support board and on an upper surface hook in loop fastening material;

two head support blocks for placement on a left side and a right side of a patient's head leaving the patient's ears uncovered, the head support blocks covered with a layer of hook in loop fastening material complementary to the hook in loop fastening material on the upper surface of the support cushion; and a strap for further immobilizing a patient's head by extending from an upper end of a first head support block across a patient's forehead to an upper end of a second head support block, the strap bearing hook in loop fastening material complementary to hook in loop fastening material on the upper ends of the head support blocks for affixing the strap to the blocks.

7. The system of claim 6, wherein the adhesive layer is covered by a protection strip that can be pulled to uncover the adhesive layer after the support cushion is correctly located without disturbing the support cushion.

8. The system of claim 6, wherein the support cushion is between 1 and 2 cm in thickness.

9. A method for immobilizing a patient's head when the patient is carried on a backboard comprising the steps of:

placing the patient face up on the backboard;

placing a head support cushion between the patient's head and the backboard to elevate the patient's head by at least one centimeter;

activating an adhesive means on the head support cushion to affix the cushion to the backboard without disturbing either the head support cushion or the patient's head;

placing head support blocks on either side of the patient's head, the head support blocks equipped with a fastening means for adhering tightly to the head support cushion while leaving the patient's ears uncovered; and securing the patient's head by attaching a first end of a forehead strap to a first head support block, running the strap over the patient's forehead and attaching a second end of the forehead strap to a second head support block.

* * * * *